(12) United States Patent
Wheland et al.

(10) Patent No.: US 6,700,023 B1
(45) Date of Patent: Mar. 2, 2004

(54) LOW TEMPERATURE INITIATORS FOR FLUOROOLEFIN POLYMERIZATION

(75) Inventors: Robert Clayton Wheland, Wilmington, DE (US); Ming-Hong Hung, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/049,409

(22) PCT Filed: Aug. 24, 2000

(86) PCT No.: PCT/US00/23222

§ 371 (c)(1),
(2), (4) Date: Feb. 6, 2002

(87) PCT Pub. No.: WO01/16100

PCT Pub. Date: Mar. 8, 2001

Related U.S. Application Data

(60) Provisional application No. 60/151,455, filed on Aug. 30, 1999.

(51) Int. Cl.$^7$ ............................................. C07C 409/00
(52) U.S. Cl. ...................... 568/560; 526/214; 526/250; 526/227
(58) Field of Search ................................ 526/227, 214, 526/250; 568/560

(56) References Cited

U.S. PATENT DOCUMENTS

| | | | | |
|---|---|---|---|---|
| 4,861,845 A | * | 8/1989 | Slocum et al. ................. 526/68 |
| 5,021,516 A | * | 6/1991 | Wheland ..................... 525/403 |
| 5,597,880 A | * | 1/1997 | Abusleme et al. .......... 526/247 |
| 5,763,552 A | * | 6/1998 | Feiring et al. .............. 526/214 |
| 5,831,131 A | * | 11/1998 | Krespan et al. ............. 568/560 |
| 5,962,746 A | * | 10/1999 | Diffendall et al. .......... 568/560 |

* cited by examiner

Primary Examiner—David W. Wu
Assistant Examiner—Henry Hu

(57) ABSTRACT

A new class of low temperature initiators has been found, enabling fluoroolefin polymerizations at relatively low temperatures. These initiators are diacyl peroxides which allow improved productivity and product properties, as well as more favorable reaction conditions.

12 Claims, No Drawings

LOW TEMPERATURE INITIATORS FOR FLUOROOLEFIN POLYMERIZATION

This application is a 371 of PCT/US 00/23222 filed on Aug. 24, 2000 and claims the benefit of provisional application 60/151,455 filed on Aug. 30, 1999.

FIELD OF THE INVENTION

A new class of low temperature initiators has been found, $C_nF_{2n+1}(CH_2)_aCF_2(C=O)O-O(C=O)CF_2(CH_2)_bC_mF_{2m+1}$, wherein n and m are each independently 1 to 4, and a and b are each independently 1 or 2, enabling fluoroolefin polymerizations at relatively low temperatures.

TECHNICAL BACKGROUND

Diacyl peroxides of diverse structure have been patented as fluoroolefin polymerization initiators, for example,

[RO(CH$_2$CF$_2$CF$_2$O)$_n$CH$_2$CF$_2$(C=O)O—]$_2$, U.S. Pat. No. 4,663,407, issued May 1987, to Daikin Industries, [—O(C=O)CFR$_f$(C$_3$F$_6$O)$_h$(C$_2$F4O)$_m$(CF$_2$O)$_n$(C$_g$F$_{2g}$O)$_a$CFR$_f$(C=O)O—]$_x$, U.S. Pat. No. 3,882,193 (issued May 6, 1975 to Minnesota Mining and Manufacturing Company); [X(CF$_2$)$_n$(C=O)O—]$_2$, U.S. Pat. No. 3,528,954 (issued Sep. 15, 1970 to E.I. du Pont de Nemours and Company); XC$_m$F$_{2m}$(C=O)OO(C=O)C$_n$F$_{2n}$X, EP 0606 492 A1 (published Jul. 9, 1993, to Daikin Industries) and Cl$_2$FC(C=O)OO(C—O)CCl$_2$F U.S. Pat. No. 5,569,728 (issued Oct. 29, 1996, to Ausimont, SpA.). The best diacyl peroxide for a particular application can often be determined by its half-life. By "half-life" we mean the elapsed time it takes for half of the initiator in a system to decompose thermally to radicals. An initiator needs to last long enough for homogeneous mixing to occur with monomer but not so long as to make polymerization uneconomically slow. Half-lives on the order of 15 minutes to several hours are desirable.

Polymerization temperature can affect fundamental aspects of final polymer structure such as molecular weight and branching. Thus, a preferred polymerization temperature is chosen first and an initiator with an appropriate half-life chosen second. As used herein "HFPO is hexafluoropropylene oxide. For example were a polymerization's temperature set to 30° C., dimer peroxide (DP) with a half-life of 0.98 hours would be a faster and better choice than heptafluorobutyryl peroxide (4P) with a half-life of 8.8 hours (Table 1). If, however, the same polymerization needed to be run at 0° C., the half-life of DP would increase to 64 to 92 hours (Table 1), threatening an uneconomically slow process.

The potential advantages of faster, lower temperature initiation include increased productivity, increased polymer linearity, decreased chain transfer, increased polymer molecular weight, decreased monomer oligomerization during product letdown, decreased acid fluoride end group formation in the polymer, and decreased reactor pressure in condensed media such as liquified hexafluoropropylene (HFP) or CO$_2$. The fastest (i.e., lowest temperature), well documented prior art diacyl peroxide, 1H3P, has a 16 hour half-life at 10° C. (see Table 1, J. Org. Chem., 47, 2009 (1982) and Japanese Pat. 61152653 A2, Chem. Abstracts 106:120380). Trichloroacetyl peroxide, which has been reported to have a 10 hour half-life at −3.9° C. (see U.S. Pat. No. 5,688,838) is still faster than 1H3P ("HCF$_2$CF$_2$—") but has two disadvantages. First, the —CCl$_3$ group tends to chain transfer and, second, the initiating Cl$_3$C* radical remains attached to the polymer chain as a potentially unstable end group. At 10° C., the inventive bis(2,2,5,5,5-pentafluoropentanoyl) peroxide (hereinafter "4H5P") and bis(2,2,5,5,6,6,7,7,8,8,8-undecafluorooctanoyl) peroxide (hereinafter "4H8P") initiators disclosed herein are 13 times faster and 9 times faster, respectively, than 1H3P. Holding the rate of radical generation constant, this represents a 10° C. to 20° C. advantage in polymerization temperature for the inventive peroxides of the present invention. Unlike trichloroacetyl peroxide, 4H5P and 4H8P will not introduce undesirable chlorine into either the polymer or the reaction mixture. Thus 4H5P, 4H8P, and the related peroxides disclosed herein appear particularly attractive as low temperature fluoroolefin polymerization initiators.

Commonly owned U.S. Pat. No. 5,763,552 discloses partially fluorinated surfactants of the formula R$_f$—(CH$_2$)$_m$—R'$_f$—COOM useful in the polymerization of fluorinated monomers. These surfactants are synthetic precursors, several steps removed, for many of the diacyl peroxides disclosed herein.

SUMMARY OF THE INVENTION

Disclosed in this invention are diacyl peroxides having the structure I,

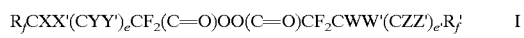

wherein e and e' are independently 0 or 1; and when e=0, at least one of X, X' is H and any of the other X, X' is H or F; when e'=0, at least one of W, W' is H and any of the other W, W' is H or F;

when e=1, at least one of X, X', Y, Y' is H and any of the other X, X', Y, Y' is H or F;

when e'=1, at least one of W, W', Z, Z' is H and any of the other W, W', Z, Z' is H or F;

wherein R$_f$=C$_n$F$_{(2n+1)}$, n=1 to 4; and wherein R$_f$=C$_m$F$_{(2m+1)}$, m=1 to 4.

Also disclosed is a method for preparing a new class of diacyl peroxides, comprising:

contacting at least one acid halide of the formula II

wherein e=0 or 1, and when e=0, at least one of X, X' is H and any of the other X, X'is H or F, and when e=1, at least one of X, X', Y, Y' is H and any of the other X, X', Y, Y' is H or F;

wherein L is Cl or F, and wherein R is R$_f$ or R$_f$; and wherein R$_f$=C$_n$F$_{(2n+1)}$, n=1 to 4 and R$_f$=C$_m$F$_{(2m+1)}$, m=1 to 4;

with a peroxide, to generate a diacyl peroxide of the structure

wherein e and e' are independently 0 or 1; and when e=0, at least one of X, X' is H and any of the other X, X' is H or F; when e'=0, at least one of W, W' is H and any of the other W, W' is H or F;

when e=1, at least one of X, X', Y, Y' is H and any of the other X, X', Y, Y' is H or F;

when e'=1, at least one of W, W', Z, Z' is H and any of the other W, W', Z, Z' is H or F;

wherein $R_f=C_nF_{(2n+1)}$, n=1 to 4; and wherein $R_{f'}=C_mF_{(2m+1)}$, m=1 to 4.

A further disclosure of this invention is a method for using a diacyl peroxide of the structure I, comprising:

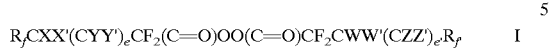
$$R_fCXX'(CYY')_eCF_2(C=O)OO(C=O)CF_2CWW'(CZZ')_{e'}R_{f'} \qquad I$$

wherein e and e' are independently 0 or 1; and when e=0, at least one of X, X' is H and any of the other X, X' is H or F; when e'=0, at least one of W, W' is H and any of the other W, W' is H or F;

when e=1, at least one of X, X', Y, Y' is H and any of the other X, X', Y,Y' is H or F;

when e'=1, at least one of W, W', Z, Z' is H and any of the other W, W', Z, Z' is H or F;

wherein $R_f=C_nF_{(2n+1)}$, n=1 to 4; and wherein $R_{f'}=C_mF_{(2m+1)}$, m=1 to 4

(i) contacting at least one diacyl peroxide having the structure I with a monomer;

(ii) optionally, in the presence of a reaction medium selected from the group consisting of fluorocarbon, chlorofluorocarbon, and hydrocarbon fluids; fluorocarbon, chlorofluorocarbon and hydrocarbon mixed with water, wherein hybrid polymerization conditions form; and liquid or supercritical carbon dioxide; and (iii) polymerizing the monomer, under suitable polymerization temperature and pressure whereby fluoroolefin polymerization occurs.

Another disclosure of this invention is a process for fluoroolefin polymerization, comprising the steps of:

(i) contacting at least one diacyl peroxide having the structure I

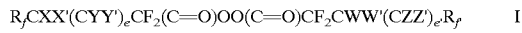
$$R_fCXX'(CYY')_eCF_2(C=O)OO(C=O)CF_2CWW'(CZZ')_{e'}R_{f'} \qquad I$$

wherein e and e' are independently 0 or 1; and when e=0, at least one of X, X' is H and any of the other X, X' is H or F; when e'=0, at least one of W, W' is H and any of the other W, W' is H or F;

when e=1, at least one of X, X', Y, Y' is H and any of the other X, X', Y, Y' is H or F;

when e'=1, at least one of W, W', Z, Z' is H and any of the other W, W', Z, Z' is H or F;

wherein $R_f=C_nF_{(2n+1)}$, n=1 to 4; and wherein $R_{f'}C_mF_{(2m+1)}$, m=1 to 4;

with a monomer;

(ii) optionally, in the presence of a reaction medium selected from the group consisting of fluorocarbon, chlorofluorocarbon, hydrocarbon fluids; fluorocarbon, chlorofluorocarbon and hydrocarbon mixed with water, wherein hybrid polymerization conditions form; and liquid or supercritical carbon dioxide; and (iii) polymerizing the monomer, under suitable polymerization temperature and pressure whereby fluoroolefin polymerization occurs.

This invention also discloses a product of the process for fluoroolefin polymerization, wherein said process comprises the steps of:

(i) contacting at least one diacyl peroxide having the structure I

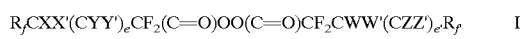
$$R_fCXX'(CYY')_eCF_2(C=O)OO(C=O)CF_2CWW'(CZZ')_{e'}R_{f'} \qquad I$$

wherein e and e' are independently 0 or 1; and when e=0, at least one of X, X' is H and any of the other X, X' is H or F; when e'=0, at least one of W, W' is H and any of the other W, W' is H or F;

when e=1, at least one of X, X', Y, Y' is H and any of the other X, X', Y, Y' is H or F;

when e'=1, at least one of W, W', Z, Z' is H and any of the other W, W', Z, Z' is H or F;

wherein $R_f=C_nF_{(2n+1)}$, n=1 to 4; and wherein $R_{f'}=C_mF_{(2m+1)}$, m=1 to 4;

with a monomer;

(ii) optionally, in the presence of a reaction medium selected from the group consisting of fluorocarbon, chlorofluorocarbon, hydrocarbon fluids; fluorocarbon, chlorofluorocarbon and hydrocarbon mixed with water, wherein hybrid polymerization conditions form; and liquid or supercritical carbon dioxide; and (iii) polymerizing the monomer, under suitable polymerization temperature and pressure whereby fluoroolefin polymerization occurs.

DETAILS OF THE INVENTION

This invention relates to the synthesis of a novel class of diacyl peroxides which are effective low temperature polymerization initiators for nonaqueous and hybrid polymerization conditions, including the use of $CO_2$ as a polymerization solvent. By "hybrid polymerization conditions" is meant mixed aqueous and non-aqueous solvents. Disclosed in the invention are diacyl peroxides of the structure

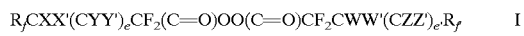
$$R_fCXX'(CYY')_eCF_2(C=O)OO(C=O)CF_2CWW'(CZZ')_{e'}R_{f'} \qquad I$$

wherein e and e' are independently 0 or 1; and when e=0, at least one of X, X' is H and any of the other X, X' is H or F; when e'=0, at least one of W, W' is H and any of the other W, W' is H or F; when e=1, at least one of X, X', Y, Y' is H and any of the other X, X', Y, Y' is H or F; when e'=1, at least one of W, W', Z, Z' is H and any of the other W, W', Z, Z' is H or F;

wherein $R_f=C_nF_{(2n+1)}$, n=1 to 4, preferably 1 or 4; and wherein $R_{f'}=C_mF_{(2m+1)}$, m=1 to 4, preferably 1 or 4.

These peroxides are synthesized from one or more acid halides of the formula

$$RCXX'(CYY')_eCF_2(C=O)L \qquad II$$

wherein e=0 or 1, and when e=0, at least one of X, X' is H and any of the other X, X' is H or F, and when e=1, at least one of X, X', Y, Y' is H and any other of the other X, X', Y, Y' is H or F;

wherein L is Cl or F, and wherein R is $R_f$ or $R_{f'}$ as described above.

For example starting with two different acid halides $R_fCXX'(CYY')_eCF_2(C=O)L$ gives not only the two symmetrical peroxides but the unsymmetrical peroxides as well. The acid chlorides or acid fluorides are subsequently reacted with peroxides such as, but not limited to, $H_2O_2$ in the presence of a base, $Na_2O_2$, and $K_2O_2$ to form the desired peroxide compounds. Examples of useful bases are, but not limited to, NaOH, KOH, $Na_2CO_3$, and $K_2CO_3$. This is demonstrated in the Examples below. When increased peroxide solubility in the reaction solvent is desired, mixtures of two or more acid halides can be used. The product in such cases includes unsymmetrical peroxides.

The preparation of initiators of this invention can be facilitated by a variety of processes, including high intensity mixing processes as described in U.S. Pat. No. 5,831,131, incorporated herein by reference. High intensity ultrasonic mixing was used to make the peroxides of Examples 1B, 2B and 2C described below. One advantage of ultrasonic mixing is the simplicity and speed of the synthetic method. Other synthetic methods can also be used, including stirring as disclosed in Z. Chengxue et al., *J. Org. Chem.*, 47, 2009 (1982), and making a nearly waterfree slurry as disclosed in U.S. Pat. No. 5,021,516. Any of the synthetic methods commonly used to make diacyl peroxides generally from acid halides can be used in the present invention. A general reference describing these methods is found in S. R. Sandler and W. Karo, *Polymer Syntheses*. Vol. 1, Academic Press, New York, 1974, Chapter 14.

Considering that 2, 3, 4, and 5, defined below in Table 2, decompose much faster than 4P 7, we conclude that having C-H bonds two or three carbons removed from the peroxide carbonyl greatly accelerates peroxide decomposition.

Vinyl monomers are generally useful for polymerization according to this invention. Preferably, these monomers are fluorocarbon, chlorofluorocarbon and hydrofluorocarbon vinyl olefins or vinyl ethers that homopolymerize, copolymerize, or copolymerize with hydrocarbon monomers such as ethylene and propylene, which are known to copolymerize with fluoroolefins. The monomers tetrafluoroethylene (TFE), perfluoropropylene vinyl ether) (PPVE), perfluoro(methyl vinyl ether) (PMVE), perfluoro(ethyl vinyl ether) (PEVE), 4,5-difluoro-2,2-bis(trifluoromethyl)-1,3-dioxole(PDD), hexafluoropropylene (HFP), $CF_2=CFOCF_2CF(CF_3)OCF_2CF_2SO_2F$ (PSEPVE) and $CF_2=CFOCF_2CF_2SO_2R$, vinylidene fluoride ($VF_2$), vinyl fluoride, trifluoroethylene, $CF_2=CFOCF_2CFCF_3OCF_2CF_2CN$ (8-CNVE), chlorotrifluoro ethylene (CTFE), $(CF_3)_2C=CH_2$, and vinyl acetate (VAc) are most preferably employed.

A variety of polymer products can be formed from the monomers employed. These are well known to those skilled in the art. See, for example, Kirk-Othmer *Encyclopedia of Chemical Technology*, 4$^{th}$ edition, Wiley-Interscience, New York, 1994, Vol. 11, pp. 621–729; H. Mark et al, *Encyclopedia of Polymer Science and Engineering*, 2$^{nd}$ edition, Wiley-Interscience, New York, 1987, Vol. 7, pp. 256–269 and 1989, Vol. 16, pp. 577–640; and J. Schiers, ed., *Modern Fluoropolymers*, John Wiley and Sons, New York, 1997.

The processes of this invention can take place in a variety of reaction media. These media include fluorocarbon, chlorofluorocarbon and hydrocarbon fluids; fluorocarbon, chlorofluorocarbon and hydrocarbon fluids mixed with water to form hybrid polymerization conditions; and liquid and supercritical carbon dioxide.

The diacyl peroxides of the present invention permit fluoroolefin polymerizations at lower temperatures. The initiation temperatures for the reactions of the present invention can range from about –20° C. to 30° C., preferably –10° C. to 20° C., and most preferably 0° C. to 10° C.

The polymerization process of the present invention offers a number of potential advantages, including increased productivity, increased linearity, faster reaction time, increased molecular weight, decreased monomer oligomerization during letdown, decreased acid fluoride end group formation, and decreased reactor pressure in condensed media such, as liquified HFP or $CO_2$.

Peroxide Titration

The peroxide titration Bused in the Examples follows. In a loosely stoppered Erlenmeyer flask several grams of dry ice are added to 25 ml of glacial acetic acid, so as to flush oxygen from the system. Five ml of a solution of 30 g of KI in 70 ml of deoxygenated water was added, and then 5.0 ml of the peroxide solution to be analyzed. The mixture was stirred for 30 minutes to allow the peroxide to react with the iodide. One hundred ml of deoxygenated water was added and the deep iodine color was titrated to light yellow with 0.1 N sodium thiosulfate. Then 0.5 g of "Thyodene" (purchased from Fisher Scientific Co.) iodometric indicator was added making the reaction mixture turn blue. Titration was completed by bringing to a colorless endpoint with additional 0.1 N sodium thiosulfate. Molar peroxide concentration was calculated by multiplying 0.01 by the total number of ml of sodium thiosulfate solution.

EXAMPLES

Unless otherwise specified, all chemicals and reagents were used as received from Aldrich Chemical Company, Milwaukee, Wis.

Example 1

Preparation and Use of 4H8P 3

The starting material for this example, 2,2,5,5,6,6,7,7,8,8-Undecafluorooctanoic acid, was prepared by the method described in U.S. Pat. No. 5,763,552, incorporated herein by reference.

A. Preparation of $CF_3CF_2CF_2CF_2CH_2CH_2CF_2(C=O)Cl$, 2,2,5,5,6,6,7,7,8,8,8-undecafluorooctanoyl chloride, ($C_4F_9$-$CH_2CH_2$-$CF_2$-COCl) (4H8Cl):

2,2,5,5,6,6,7,7,8,8,8-Undecafluorooctanoic acid (50 g, 0.146 mol) was dissolved in methylene chloride (250 mL). Pyridine (4.62 g, 0.0584 mol) and oxalyl chloride (22.3 g, 0.175 mol) were added in sequence, a slight exotherm was observed. The reaction mixture was refluxed for overnight (ca. 16 hrs) and the methylene chloride solvent was removed in vacuo after cooling. Ether was then added into the residue and the solution was filtered to remove the insoluble solid salt. After removing the ether solvent the residue was distilled to afford the title compound as a clear, colorless liquid, bp. 41–42° C./10 mm Hg, yield 29.5 g (56%); repeated run gave a 70% yield. $^1$H NMR (500 MHz, CDCl$_3$): δ 2.39 (m, 2H), 2.47 (m, 2H); $^{19}$F NMR (282.75 MHz, CDCl$_3$): –81.6 (m, 3F), –103.2 (t, J=15.8 Hz, 2F), –115.2 (t, J=14.8 Hz, 2F), –124.7 (m, 2F), –126.5 (m, 2F); IR (neat): 1800cm$^{-1}$. Anal. Calcd. for $C_8H_4F_{11}ClO$: C: 26.65, H: 1.12, Cl: 9.83; Found: C: 26.61, H: 1.07, Cl: 9.66; Mass for [M-COCl]: Calc: 297.0137; Found: 297.0172.

B. Preparation of 4H8P 3

A wet-ice, chilled 150 ml beaker was loaded with 1.5 g of 85% potassium hydroxide pellets (23 mmoles) dissolved in 5 ml distilled water, 78 ml of Freon® E1 ($CF_3CF_2CF_2OCFHCF_3$), and 2.35 ml of 30% aqueous hydrogen peroxide (23 mmoles). A nominal 100 watt titanium ultrasonic horn was lowered into the reaction mixture and then 6.5 g of 4H8Cl (18 mmoles) added all at once. After an additional 30 seconds of ultrasonication, the reaction mixture was transferred to a separatory funnel prechilled to ~–15° C. The lower organic phase, still a bit hazy, was quickly separated and its volume measured as 74 ml. After sitting about 10 minutes at ~0° C., iodometric titration found the concentration of 4H8P 3 to be 0.076 M for a yield of 62% based on starting acid chloride 4H8Cl.

C. Initiation of TFE Polymerization, Nonaqueous Fluorocarbon Solvent

A prechilled 400 ml autoclave was loaded with 100 ml Freon® 113 ($CF_2ClCCl_2F$) and 5 ml of the 0.076 M 4H8P 3 solution prepared above. The autoclave was evacuated, filled with 50 g of tetrafluoroethylene (TFE) and allowed to warm towards room temperature. After initial loading at 82 psi at −44° C., pressure steadily dropped during warm up hitting 56 psi at −15° C. and 24 psi at 23° C. at the end of the warmup ~10 hours later. Filtration, washing, and drying gave 43 g of white poly(tetrafluoroethylene).

D. Initiation of TFE/PPVE Copolymerization, Nonaqueous Fluorocarbon
Solvent

A prechilled 400 ml autoclave was loaded with 100 ml Freon® 113 ($CF_2ClCCl_2F$) and 5 ml of the 0.076 M 4H8P 3 solution prepared above. The autoclave was evacuated, filled with 50 g of tetrafluoroethylene (TFE) and 5 g of perfluoro(propyl vinyl ether) and allowed to warm towards room temperature. After initial loading at 125 psi at −35° C., pressure decreased to 106 psi at 7° C. and finished at 22 psi at 24° C. at the end of the warmup ~10 hours later. Filtration, washing, and drying gave 48.6 g of white tetrafluoroethylene/perfluoro(propyl vinyl ether) copolymer.

E. Initiation of TFE Polymerization Mixed Aqueous/Fluorocarbon Solvent

A prechilled 400 autoclave was loaded with 100 ml ice cold water and 5 ml of 0.095 M 4H8P 3 solution in $CF_3CF_2CF_2OCFHCF_3$. The autoclave was evacuated, filled with 50 g of tetrafluoroethylene (TFE) and allowed to warm towards room temperature. After initial loading at 230 psi at −0.3° C., pressure steadily dropped during warm up hitting 178 psi at 19° C. and 32 psi at 30° C. at the end of the warmup ~7 hours later. Filtration, washing, and drying gave 43 g of white poly(tetrafluoroethylene).

Example 2

Preparation and Use of 4H5P 2
Chemical Equations

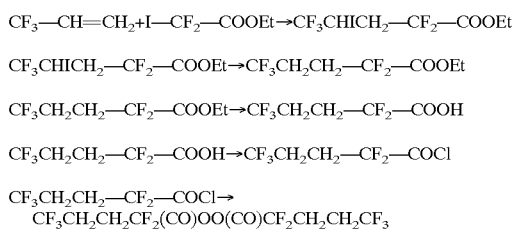

A. Preparation of ethyl 4-iodo-2,2,5,5,5-pentafluoropentanoate

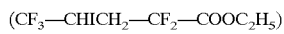

In a 400 mL stainless steel autoclave was charged 3,3,3-trifluoro-1-propene ($CF_3$—CH=$CH_2$, 42 g, 0.42 mol) and ethyl iododifluoroacetate (I—$CF_2$—$COOC_2H_5$, 100 g, 0.40 mol). The tube was sealed and heated at 200° C. for 8 hr under agitation. After cooling the product mixture was distilled to afford the title product as a clear, pale pink liquid. Yield 96 g (69.4%), bp. 47–50° C./1 mm Hg. $^1$H NMR (500 MHz, CDCl$_3$): δ 4.42 (m, 1H), 4.35 (q, J=7 Hz, 2H), 3.03 (m, 1H), 2.96 (m, 1H), 1.40 (t, J=7 Hz, 3H); $^{19}$F NMR (282.75 MHz, CDCl$_3$): −70.5 (dm, 3F), −105.8 (qm, 2F).

B. Preparation of ethyl 2,2,5,5,5-pentafluoropentanoate

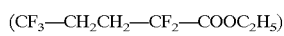

The compound ethyl 4-iodo-2,2,5,5,5-pentafluoropentanoate prepared from above experiment (86.5 g, 0.25 mol) was added dropwise into a well-stirred tributyltin hydride liquid (75.5 g, 0.26 mol). The reaction temperature was controlled at below 30° C. with external cooling during the process. After addition was complete, the mixture was stirred at 50° C. for 2 hr. The product was isolated by distillation, 42.0 g (76.4% yield) of product was obtained as a clear, colorless liquid, bp. 38–39° C./10 mm Hg. $^1$H NMR (500 MHz, CDCl$_3$): δ 4.35 (q, J=7 Hz, 2H), 2.35 (m, 4H), 1.38 (t, J=7 Hz, 3H); $^{19}$F NMR (282.75 MHz, CDCl$_3$): −67.3 (m, 3F), −107.5 (m, 2F).

C. Preparation of 2,2,5,5,5-pentafluoropentanoic acid

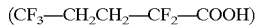

Ethyl 2,2,5,5,5-pentafluoropentanoate (140 g, 0.636 mol) was mixed with concentrated hydrochloric acid (350 mL) under nitrogen atmosphere, and was heated at 100–110° C. under vigorous stirring. The progress of the reaction was monitored by gas chromatography and the reaction was stopped after 72 hrs. After cooling the bottom organic layer was separated and distilled to afford the desired acid product (104 7 g, 86% yield) as a clear, colorless liquid, bp. 68–69° C./10 mm Hg. $^1$H NMR (500 MHz, CDCl$_3$): δ 10.60 (s, 1H, —COOH), 2.20 (m, 4H); $^{19}$F NMR (282.75 MHz, CDCl$_3$): −67.4 (t, J=9 Hz, 3F), −108.2 (m, 2F).

D. Preparation of $CF_3CH_2CH_2CF_2(C=O)Cl$, 2,2,5,5,5-pentafluoropentanoyl chloride; ($CF_3$—$CH_2CH_2$—$CF_2$—COCl)(4H5Cl)

2,2,5,5,5-pentafluoropentanoic acid (96 g, 0.5 mol) was dissolved in methylene chloride (400 mL). Pyridine (15.8 g, 0.2 mol) and oxalyl chloride (76.2 g, 0.6 mol) were slowly added in sequence into the above solution while the reaction temperature was kept at ≦25° C. After the addition was complete, the reaction mixture was stirred at ambient temperature for 48 hrs. The methylene chloride solvent was removed by distillation and vacuum was applied so that the volatile product was separated from the residue and was collected in a dry ice-acetone bath cold trap. Re-distillation gave the desired compound as a clear, colorless liquid, bp. 95–97° C., yield 65 g (62%). $^1$H NMR (500 MHz, CDCl$_3$): δ 2.40 (m, 4H); $^{19}$F NMR (282.75 MHz, CDCl$_3$): −64.9 (t, J=9.4 Hz, 3F), −100.6 (m, 2F).

E. Preparation of 4H5P 2 in $CF_3CF_2CF_2OCFHCF_3$

A wet-ice/acetone chilled 150 ml beaker was loaded with 3.17 g of potassium carbonate (23 mmoles) dissolved in 5 ml distilled water, 78 ml of Freon® E1 ($CF_3CF_2CF_2OCFHCF_3$), and 2.35 ml of 30% aqueous hydrogen peroxide (23 mmoles). A nominal 100 watt titanium ultrasonic horn was lowered into the reaction mixture now chilled to −2° C. and then 4.20 g of 4H5Cl (20 mmoles) added all at once. After an additional 60 seconds of ultrasonication, the reaction mixture had reached 10° C. and was transferred to a separatory funnel prechilled to ~31 15° C. The lower organic phase, still a bit hazy, was separated and its volume measured as 74 ml. Iodometric titration found the concentration of 4H5P 2 to be 0.102 M for a yield of 75% based on starting acid chloride 4H5Cl.

F. Preparation of 4H5P 2 in $CF_3CFHCFHCF_2CF_3$

A wet-ice/acetone chilled 150 ml beaker was loaded with 3.17 g of potassium carbonate (23 mmoles) dissolved in 5 ml distilled water, 78 ml of $CF_3CFHCFHCF_2CF_3$, and 2.35 ml of 30% aqueous hydrogen peroxide (23 mmoles). A nominal 100 watt titanium ultrasonic horn was lowered into the reaction mixture now chilled to −5° C. and then 4.20 g of 4H5Cl (20 mmoles) added all at once. After an additional 45 seconds of ultrasonication, the reaction mixture was transferred to a separatory funnel prechilled to ~−15° C. The lower organic phase, milky white in appearance, was separated and its volume measured as 74 ml. Iodometric titration found the concentration of 4H5P 2 to be 0.107 M for a yield of 79% based on starting acid chloride 4H5Cl.

G. Use of Trifluoroacetic Acid to Clear Peroxide Solution

The solution made in part C above was milky in appearance and has to be used immediately if precipitates are to be avoided over the course of long-term, low-temperature storage. Adding trifluoroacetic acid causes most of the haze to clear. A 0.107 M 4H5P solution diluted down with 20% its volume of trifluoroacetic acid stayed clear at −78° C. for the 15–30 minutes required to set up for polymerization experiments G and H below.

Adding trifluoroacetic acid appears to speed up the rate of peroxide thermal decomposition. Fifteen milliliters of trifluoroacetic acid were added to 64 ml of the 0.107 M 4H5P solution prepared above in part C causing the milky solution to go largely clear. This mixture was maintained at 0° C. in a constant temperature bath while samples were periodically withdrawn for iodometric titration with the results shown below in Table 1.

TABLE 1

| Time, second | Molarity, 4H5P 2 | Nominal Half-Life |
|---|---|---|
| 0 | 0.107 | |
| 1800 | 0.085 | 1.5 hr |
| 3600 | 0.063 | 1.3 hr |
| 7200 | 0.046 | 1.6 hr |
| 10800 | 0.040 | 2.1 hr |
| 18300 | 0.030 | 2.7 hr |

Treating each peroxide titration as a single point in first-order kinetics, half-life starts off at about 1.5 hours and then drifts to longer times. Polymerization is still initiated after dilution of the peroxide solution with trifluoroacetic acid (see Parts J and K below).

H. Initiation of TFE Polymerization, Carbon Dioxide Reaction Medium

An autoclave prechilled to −37° C. was loaded with 5 ml of 0.107 M 4H5P 2 in $CF_3CFHCFHCF_2CF_3$ solvent. The autoclave was evacuated, filled with 50 g of tetrafluoroethylene (TFE) and 150 g of carbon dioxide and allowed to warm towards room temperature. The autoclave was shaken overnight passing through a maximum of 1131 psi at 31° C. Venting gave poly(tetrafluoroethylene) as a white powder that weighed 41.8 g after drying over a weekend in a 150° C. vacuum oven.

I. Initiation of TFE/E Polymerization, Carbon Dioxide Reaction Medium

An autoclave prechilled to −42° C. was loaded with 5 ml of 0.107 M 4H5P 2 in $CF_3CFHCFHCF_2CF_3$ solvent. The autoclave was evacuated, filled with 50 g of tetrafluoroethylene (TFE), 14 g of ethylene, and 150 g of carbon dioxide and allowed to warm towards room temperature. The autoclave was shaken overnight passing through a maximum of 1010 psi at 31° C. Venting gave white polymer that weighed 39.5 g after drying over a weekend in a 150° C. vacuum oven.

J. Initiation of TFE Polymerization, Carbon Dioxide Reaction Medium, $CF_3COOH$ Added to Initiator Solution An autoclave prechilled to −44° C. was loaded with 5 ml of 0.105 M 4H5P 2 in $CF_3CFHCFHCF_2CF_3$ solvent to which 1.25 ml of $CF_3COOH$ had been added to eliminate haze and precipitates. The autoclave was evacuated, filled with 50 g of tetrafluoroethylene (TFE) and 150 g of carbon dioxide and allowed to warm towards room temperature. The autoclave was shaken overnight passing through a maximum of 1084 psi at 28° C. Venting gave poly(tetrafluoroethylene) as a white powder that weighed 38.7 g after drying over a weekend in a 150° C. vacuum oven.

K. Initiation of TFE/E Polymerization, Carbon Dioxide Reaction Medium, $CF_3COOH$ Added to Initiator Solution An autoclave prechilled to −56° C. was loaded with 5 ml of 0.105 M 4H5P 2 in $CF_3CFHCFHCF_2CF_3$ solvent to which 1.25 ml of $CF_3COOH$ had been added to eliminate haze and precipitates. The autoclave was evacuated, filled with 50 g of tetrafluoroethylene (TFE), 14 g of ethylene, and 150 g of carbon dioxide and allowed to warm towards room temperature. The autoclave was shaken overnight passing through a maximum of 1095 psi at 29° C. Venting gave white polymer that weighed 15.3 g after drying over a weekend in a 150° C. vacuum oven.

Example 3

Thermal Decomposition of Initiators at Different Temperature

When n and m are both 1, structure I may be represented by the designation 4H5P (2). When both n and m are 4, structure I may be represented by the designation 4H8P (3). Both of these peroxides demonstrate very short half-lives compared to the initiators currently used in fluorocarbon polymerization.

Half-lives of initiators are generally determined by placing the peroxide solution in a constant temperature bath and following the peroxide concentration as a function of time by iodometric titration. The initiator 4H5P has a half-life of 4.4 hr at 0° C., and the initiator 4H8P has a half-life of 7.1 hr at 0° C. These are much shorter than the half-lives of initiators currently used in fluorocarbon polymerization. Examples of the currently-used initiators are heptafluorobutyryl peroxide (4P), which has a 4.3 hr. half-life at 25° C., and HFPO dimer peroxide (DP, structure 6 in Table 2), which has a 0.98 hr half-life at 30° C. These results are summarized in Table 2 below.

TABLE 2

THERMAL DECOMPOSITION OF $R_f(C=O)OO(C=O)R_f^1$

| # | $R_f$ GROUP ($R_f$ and $R_f^1$ are the same) | NAME | 0° C. Half-life | 10° C. Half-life | 15° C. Half-life | 25° C. Half-life | 30° C. Half-life | REF |
|---|---|---|---|---|---|---|---|---|
| 2 | $CF_3CH_2CH_2CF_2$— | 4H5P | 4.4 hr | 1.2 hr | | | | 1 |
| 3 | $C_4F_9CH_2CH_2CF_2$— | 4H8P | 7.1 hr | 1.7 hr | | | | 2 |
| 4 | $HCF_2CF_2$— | 1H3P | | | | 0.85 hr | 0.46 hr | 3 |
| | | | | | 16 hr | | | 5 |
| 5 | $H_2CFCF_2$— | 2H3P | | | | 0.7 hr | | 4 |
| 6 | $CF_3CF_2CF_2OCF(CF_3)$— | DP | | | | | 0.98 hr | 3 |
| 7 | $CF_3CF_2CF_2$— | 4P | | | | 4.3 hr | 8.8 hr | 3 |

$^1$ $CF_3CF_2CF_2OCFHCF_3$ solvent was used in this experiment.
2 $CF_3CF_2CF_2OCFHCF_3$ solvent was used in this experiment.
3 Z. Chengxue, et. al., J. Org. Chem., 47, 2009 (1982), $CFCl_2CF_2Cl$ solvent
4 Japanese Pat. 61152653 A2, Chem. Abstracts 106:120380
5 $CF_3CF_2CF_2OCFHCF_3$ solvent was used in this experiment.

What is claimed is:

1. A diacyl peroxides having the structure I, $$R_fCXX'(CYY')_eCF_2(C=O)OO(C=O)CF_2CWW'(CZZ')_{e'}R_f' \quad I$$

wherein e and e' are independently 0 or 1; and when e=0, at least one of X, X' is H and any of the other X, X' is H or F; when e'=0, at least one of W, W' is H and any of the other W, W' is H or F;

when e=1, at least one of X, X', Y, Y' is H and any of the other X, X', Y, Y' is H or F;

when e'=1, at least one of W, W', Z, Z' is H and any of the other W, W', Z, Z' is H or F;

wherein $R_f=C_nF_{(2n+1)}$, n=1 to 4; and wherein $R_{f'}=C_mF_{(2m+1)}$, m=1 to 4.

2. The diacyl peroxide of claim 1 wherein n and m, independently, are 1 or 4.

3. A method for preparing a new class of diacyl peroxides, comprising:

contacting at least one acid halide of the formula II $$RCXX'(CYY)_eCF_2(C=O)L \quad II$$

wherein e=0 or 1, and when e=0, at least one of X, X' is H and any of the other X, X' is H or F, and when e=1, at least one of X, X', Y, Y' is H and any of the other X, X', Y, Y' is H or F;

wherein L is Cl or F, and wherein R is $R_f$ or $R_{f'}$; and wherein $R_f=C_nF_{(2n+1)}$, n=1 to 4 and $R_{f'}=C_mF_{(2m+1)}$, m=1 to 4;

with a peroxide, to generate a diacyl peroxide of the structure $$R_fCXX'(CYY')_eCF_2(C=O)OO(C=O)CF_2CWW'(CZZ')_{e'}R_f' \quad I$$

wherein e and e' are independently 0 or 1; and when e=0, at least one of X, X' is H and any of the other X, X' is H or F; when e'=0, at least one of W, W' is H and any of the other W, W' is H or F;

when e=1, at least one of X, X', Y, Y' is H and any of the other X, X', Y, Y' is H or F;

when e'=1, at least one of W, W', Z, Z' is H and any of the other W, W', Z, Z' is H or F;

wherein $R_f=C_nF_{(2n+1)}$, n=1 to 4; and wherein $R_{f'}=C_mF_{(2m+1)}$, m=1 to 4.

4. The method according to claim 3 wherein the peroxide is selected from the group consisting of $H_2O_2$ added in the presence of a base, $Na_2O_2$, and $K_2O_2$.

5. The method according to claim 4 wherein the base is selected from the group consisting of NaOH, KOH, $Na_2CO_3$, and $K_2CO_3$.

6. A method for using a diacyl peroxide of the structure I, comprising:

$$R_fCXX'(CYY')_eCF_2(C=O)OO(C=O)CF_2CWW'(CZZ')_{e'}R_f' \quad I$$

wherein e and e' are independently 0 or 1; and when e=0, at least one of X, X' is H and any of the other X, X' is H or F; when e'=0, at least one of W, W' is H and any of the other W, W' is H or F;

when e=1, at least one of X, X', Y, Y' is H and any of the other X, X', Y, Y' is H or F;

when e'=1, at least one of W, W', Z, Z' is H and any of the other W, W', Z, Z' is H or F;

wherein $R_f=C_nF_{(2n+1)}$, n=1 to 4; and wherein $R_{f'}=C_mF_{(2m+1)}$ m=1 to 4

(i) contacting at least one diacyl peroxide having the structure I with a monomer;

(ii) optionally, in the presence of a reaction medium selected from the group consisting of fluorocarbon, chlorofluorocarbons and hydrocarbon fluids; fluorocarbon, chlorofluorocarbon and hydrocarbon mixed with water, wherein hybrid polymerization conditions form; and liquid or supercritical carbon dioxide; and (iii) polymerizing the monomer, under suitable polymerization temperature and pressure whereby fluoroolefin polymerization occurs.

7. The method of claim 6 wherein, independently, n=1 or 4 and m=1 or 4; e=1; e'=1; and X, X', Y, Y', W, W', Z and Z' are all H.

8. The method of claim 6 wherein the temperature is from about −20° C. to about 30° C.

9. The method of claim 6 wherein the temperature is from about −10° C. to about 20° C.

10. The method of claim 6 wherein, independently, n=1 or 4 and wherein m=1 or 4; e=1; e'1; and X, X', Y, Y', W, W', Z and Z' are all H; and wherein the temperature is from about −10° C. to about 20° C.

11. A process for fluoroolefin polymerization, comprising the steps of:

(i) contacting at least one diacyl peroxide having the structure I $$R_fCXX'(CYY')_eCF_2(C=O)OO(C=O)CF_2CWW'(CZZ')_{e'}R_f' \quad I$$

wherein e and e' are independently 0 or 1; and when e=0, at least one of X, X' is H and any of the other X, X' is H or F; when e' 0, at least one of W, W' is H and any of the other W, W' is H or F;

when e=1, at least one of X, X', Y, Y' is H and any of the other X, X', Y, Y' is H or F;

when e'=1, at least one of W, W', Z, Z' is H and any of the other W, W', Z, Z' is H or F;

wherein $R_f=C_nF_{(2n+1)}$, n=1 to 4; and wherein $R_{f'}=C_mF_{(2m+1)}$, m 1 to 4; with a monomer;

(ii) optionally, in the presence of a reaction medium selected from the group consisting of fluorocarbon, chlorofluorocarbon, hydrocarbon fluids; fluorocarbon, chlorofluorocarbon and hydrocarbon mixed with water, wherein hybrid polymerization conditions form; and liquid or supercritical carbon dioxide; and (iii) polymerizing the monomer, under suitable polymerization temperature and pressure whereby fluoroolefin polymerization occurs.

12. A product of the process of claim 11.

* * * * *